United States Patent [19]
Libin

[11] Patent Number: 5,855,872
[45] Date of Patent: *Jan. 5, 1999

[54] COMPOSITIONS FOR TREATING HERPES SIMPLEX VIRUS INFECTIONS

[76] Inventor: Barry M. Libin, 15 Thornhedge Rd., Bellport, N.Y. 11713

[ * ] Notice: The term of this patent shall not extend beyond the expiration date of Pat. No. 5,671,668.

[21] Appl. No.: 934,327

[22] Filed: Sep. 19, 1997

Related U.S. Application Data

[63] Continuation-in-part of Ser. No. 798,504, Feb. 10, 1997, which is a continuation-in-part of Ser. No. 51,861, Apr. 26, 1993, which is a division of Ser. No. 901,679, Jun. 22, 1992, Pat. No. 5,236,699.

[51] Int. Cl.$^6$ .............................. A61K 7/16; A61K 7/22; A61K 31/055; A61K 31/14
[52] U.S. Cl. ................................................ 424/49; 424/54
[58] Field of Search .......................................... 424/49–88

[56] References Cited

U.S. PATENT DOCUMENTS

| | | | |
|---|---|---|---|
| 5,158,699 | 10/1992 | MacGilip et al. | 252/132 |
| 5,236,699 | 8/1993 | Libin | 414/54 |
| 5,328,682 | 7/1994 | Pullen et al. | 424/49 |
| 5,348,738 | 9/1994 | Takatsuka et al. | 424/49 |
| 5,362,737 | 11/1994 | Vora et al. | 514/291 |
| 5,447,923 | 9/1995 | Catrenich et al. | 514/147 |
| 5,500,448 | 3/1996 | Cummins et al. | 424/49 |
| 5,503,822 | 4/1996 | Schulman | 424/49 |
| 5,578,315 | 11/1996 | Chien et al. | 424/435 |
| 5,607,681 | 3/1997 | Garey et al. | 424/409 |

FOREIGN PATENT DOCUMENTS

| | | |
|---|---|---|
| 680745A2 | 8/1995 | European Pat. Off. . |
| 97/00667A1 | 1/1997 | WIPO . |
| 97/00668A1 | 1/1997 | WIPO . |
| 97/49383A1 | 12/1997 | WIPO . |

OTHER PUBLICATIONS

Drug Launches Dentyl PH The Fresh Breath Company United Kingdom Jul. 1997—Liquid Oral Tropical: Cetylpyridinium CL, Trillosan, Mint Oil Clove Oil, Nov. 17, 1997.

Drug Launches Antebor–N So Dip Switzerland May 1995 Topical Antiacne Preparation for Acne Seboorone Chlorhexidine 0.3% Triclosan 0.69%, Aug. 21, 1995.

Drug Launches Hexacorton Cream Orva Turkey 3rd Qtr–1991 Topical Corticosteroid Combinations Prednisolone 21 Acetate 5% Triclosan 3% Chlorohexidine HCG 2%, Mar. 30, 1992.

Skaari et al Jl. Clin. Periodont. 23(8):778–781 Aug. 1996 "Mouthrinses Contains Tricosan Reduce the Incideme of Recurrent Aphthous Ulcers" (RAV).

Addy et al. Jl. Clin. Periodont. 4(5):108–116 Dec. 1977 "Hibitane in the Treatment of Aphthous Ulceration".

*Primary Examiner*—Shep K. Rose
*Attorney, Agent, or Firm*—Michael Ebert

[57] ABSTRACT

A composition for treating diseased tissues resulting from a herpes simplex virus infection. When in ointment form, the composition has dispersed in an oil and water emulsion two distinct antimicrobial agents, one being Triclosan which is non-cationic and water insoluble, the Triclosan being solubilized by a solubilizer. The second antimicrobial agent which is cationic and water-soluble, is combined with the solubilized Triclosan to produce an antimicrobial composite that is polar and retained by the diseased tissues to which it is applied.

10 Claims, No Drawings

COMPOSITIONS FOR TREATING HERPES SIMPLEX VIRUS INFECTIONS

RELATED APPLICATIONS

This application is a continuation-in-part of the Libin application Ser. No. 08/798,504 filed Feb. 10, 1997 entitled "BACTERIAL COMPOSITION COMBINING TWO ANTIBACTERIAL AGENTS," which in turn is a continuation-in-part of the Libin application Ser. No. 08/051,861, filed Apr. 26, 1993 entitled "ANTIPLAQUE MOUTH RINSE," this being a division of the earlier Libin application Ser. No. 901,679, filed Jun. 22, 1992, now Pat. No. 5,236,699. The disclosures of these prior Libin applications are incorporated herein by reference.

BACKGROUND OF INVENTION

1. Field of Invention

This invention relates generally to a composition for treating diseased tissues resulting from a herpes simplex virus infection, and more particularly to a composition that can be applied topically to the diseased tissue and includes a composite in which two distinct antimicrobial agents are synergistically combined, one being non-cationic, the other cationic.

2. Status of Prior Art

My above-identified copending application discloses a bactericidal composition combining two antibacterial agents for treating diseased tissue infected by pathogenic bacteria. One agent is non-cationic Triclosan which is substantially insoluble in water. The other agent is cationic, such as cetylpyridinium chloride or chlorhexidine. Also included is a solubilizer for the Triclosan.

The two agents coact synergistically, for the resultant bactericidal composition is far more effective than either agent acting alone. Because the combined agents carry a polar charge, the composition is readily adsorbed by the tissue to which it is applied and is retained thereby for a prolonged period. The combined agents are not released from the tissue by saliva or other natural fluids to which the tissues are exposed. Hence the composition exhibits a high degree of substantivity.

The composition which combines non-cationic Triclosan with a cationic antibacterial agent, when used to treat diseased tissues in the oral cavity of a patient, are in the form of a mouth rinse which bathes these tissues.

The present invention which makes use of a similar composition in an ointment or salve form that can be applied topically is based as the discovery that a composite of the same two bactericidal agents is effective against a herpes simplex virus infection which because it is viral in nature normally does not respond to treatment by bactericidal agents.

There are two existing types of herpes simplex virus infections (HSV), each type having multiple strains. HSV-Type 1 infects mucous membranes of the oral cavity as well as perioral skin, the skin above the waist and the eyes. A serious HSV-Type 1 infection is herpes keratitis which may result in disfunction of the cornea. Other primary HSV-Type 1 infections include stomatitis and dermatitis.

HSV-Type 2 causes genital infections and is the second most common venereal disease not only in the United States but in many other countries.

It has been found that when the immune system is compromised as in the case of patients undergoing chemotherapy for cancer, the patients then become highly susceptible to herpes simplex virus infections.

A large percentage of the United States population is affected by some form of a herpes virus infection, there being an estimated 98 million cases occurring each year of herpes labialis (HSV-Type 1). And in the case of genital herpes (HSV-Type 2), there are about 30 million cases each year.

HSV-Type 1 resides in latent form in the trigeminal ganglions in the facial area. In some individuals this virus remains inactive while in many others the virus may travel from the nerves located near the cheek bone to the lips. This gives rise to vesiculo-ulcerative eruptions around the lips, the chin and the cheeks, or under the nose.

Herpes simplex virus consists of evolving strains that are resistant to known antiviral agents, such as geniciclevir and acylovir. Because HSV infections are not treatable by known antiviral agents, the usual protocol for such infections includes the elimination of the conditions which precipitated the viral infections and local antibiotic treatment to prevent bacterial infections at the site of the viral infection. But an antibiotic, such as penicillin is a bactericidal agent and as such is ineffective against a HSV infection.

SUMMARY OF INVENTION

In view of the foregoing, the main object of this invention is to provide a composition which includes a composite that synergistically combines the actions of two antimicrobial agents that is effective in the treatment of herpes simplex virus infections.

More particularly, an object of this invention is to provide a composition of the above type in which one antimicrobial agent in the composite is non-cationic Triclosan and the other a cationic agent whereby the composite carries an ionic charge that promotes polar adsorption of the composite by HSV infected tissues, thereby bringing about potentiated adherence of the composite to the tissues and sustained antimicrobial effectiveness and a high degree of sustantivity.

Also an object of the invention is to provide a composition of the above type which is in the form of an ointment having the composite dispersed therein to facilitate the delivery of the composite to the diseased tissues.

Briefly stated, objects are attained by a composition for treating diseased tissues resulting from a herpes simplex virus infection. When in ointment form, the composition has dispersed in an oil and water emulsion two distinct antimicrobial agents, one being Triclosan which is non-cationic and water insoluble, the Triclosan being solubilized by a solubilizer.

The second antimicrobial agent which is cationic and water-soluble is combined with the solubilized Triclosan to produce an antimicrobial composite that is polar and retained by the diseased tissue to which it is applied. The composite is not released from the diseased tissue by exudate oozing therefrom and therefore exhibits a high degree of substantivity.

DETAILED DESCRIPTION OF INVENTION

A composition in accordance with the invention for treating a herpes simplex virus (HSV) infection is preferably in the form of a viscous ointment or salve, making it possible to coat the diseased tissues to bring the active ingredients of the ointment in contact with the tissue. However, where the location of the HSV diseased tissues lends itself to having it brushed or bathed with the active ingredients, the composition may be in a liquid or less viscous form or it may be contained in a spray dispenser.

To create a viscous ointment, de-ionized water, oil and an emulsifier are intermingled to create an emulsion. A suitable oil for the purpose is petrolatum, a mineral oil, and a suitable emulsifier is wax NF. It is also desirable to include in the ointment a preservative, such as methyl paraben or propyl paraben as well as a humectant, such as propylene glycol.

Dispersed in the emulsion is an antimicrobial composite created by two distinct antimicrobial agents, one being non-cationic and the other cationic. When combined, the agents act synergistically to promote their delivery and retention on the HSV-infected tissues.

Non-cationic antibacterial agents, which are particularly desirable in terms of effectiveness and safety, are halogenated di-phenyl ethers, preferably Triclosan. In the present composite, an effective amount of Triclosan is included, typically about 0.015 to 5.0% by weight.

Triclosan is substantially water-insoluble, meaning that its solubility is less than 1% by weight in water at 25° C. Hence the composition must include a solubilizer for the Triclosan which does not adversely affect its antimicrobial activity, the amount of the solubilizer being sufficient to solubilize the water-insoluble Triclosan. A preferred solubilizer for this purpose is sterol alcohol.

The second antimicrobial agent included in the composite is cetylpyridinium chloride (CPC), which is the monohydrate of the quaternary salt of pyridine and cetyl chloride. CPC, which is cationic, is highly soluble in water and alcohol. The percentage by weight of CPC in the composite is in the range of about 0.001 to 3%. In a preferred composite, the amount by weight of the second antimicrobial agent in the formulation is almost equal to that of Triclosan, the first agent, which is non-cationic.

We have found that in the composite combining the cationic with the non-cationic antimicrobial agent, two significant effects are obtained; the first being that the combined agents are readily adsorbed and retained on HSV diseased tissues for a relatively prolonged period and are not released by exudate oozing from the tissues.

The second effect of these two antimicrobial agents is that they are effective against HSV infected tissues even though these agents normally behave as bactericidal agents which cannot be expected to be effective against a viral infection.

Yet we have found in clinical studies that the antimicrobial non-cationic/cationic composite is effective against HSV infections. Thus in treating HSV-Type 1 lesions, the lesions are healed in the course of a relatively short period of treatment. Also less pain is experienced, for the composite has an analgesic and as well as an anti-inflammatory effect.

While the mechanism by which the composite serves to treat an HSV infection is not fully understood, it is believed that the composite acts to lower the pH to non-physiologic levels, resulting in the destruction of the viral envelope and the loss of infectivity. Also the anti-inflammatory effect of the composite appears to interfere with viral activity. The anti-inflammatory effects of Triclosan are believed to play a vital role in the treatment of lesions produced by HSV infections. The precursor of a lesion is severe inflammation of the tissues, this causing laceration of the tissues to create a lesion. Triclosan has been found to inhibit prostaglandin, lipids which occur in body tissues, as well as to inhibit leukotriene, a lipid compound related to prostaglandin known to mediate the inflammatory response. The Triclosan-CPC composite which is retained by the diseased tissues to which it is applied, acts to alleviate inflammation of these tissues and to discourage the progressive enlargement of the lesion.

As a consequence, inflammation surrounding the HSV lesion is markedly reduced and the lesion is rendered inert; thereby bringing about a significant improvement in the condition of the subject being treated.

HSV infections, such as genital herpes (HSV-Type 2) generally develop a few days after exposure, resulting in fluid-filled blisters. Treating of these blisters with an ointment in accordance with the invention, causes the blisters to rupture and exude the fluid. But this exudate does not wash away the composite, for the composite adheres to the diseased tissues.

The reason this happens is that the combined non-cationic/cationic agents carry a polar charge, causing the composite to be adsorbed by the tissue to which it is applied and to be retained by the tissues for a prolonged period.

While CPC is a preferred water-soluble cationic antibacterial agent and provides distinct advantages, usable in place of CPC in combination with Triclosan are such water-soluble cationic antibacterial agents as chlorhexidine and domiphen bromide, a quaternary salt. Chlorhexidine has been found to be particularly effective when combined with Triclosan. The following table provides a list of the ingredients included in an ointment in accordance with the invention.

| # | INGREDIENT | % BY WEIGHT |
|---|---|---|
| 1. | De-ionized water | 30–45 |
| 2. | Petrolatum | 10–40 |
| 3. | Emulsifying wax NF | 0.10–10 |
| 4. | Methyl Paraben | 0.05–0.4 |
| 5. | Propyl Paraben | 0.05–1.0 |
| 6. | Propylene Glycol | 2.0–20 |
| 7. | Triclosan | 0.10–5.0 |
| 8. | Sterol Alcohol | 10–40 |
| 9. | Cetyl Pyridinium Chloride or Chlorhexidine | 0.001–3.0 |

Other Applications

A composition in accordance with the invention includes an inert antimicrobial agent (e.g., Triclosan; Germyl-115; phenoxy ethanol) in combination with a cationic agent (e.g., cetyl pyridinium chloride; chlorohexidine; domaphen bromide). The combination of non-cationic and cationic agents produces a polar charge causing the composite to be adsorbed by the tissues being treated, thereby imparting greater substantivity to the drug and enhancing its effectiveness.

Or the composite may combine an anionic antimicrobial agent (e.g., potassium sorbate; sodium benzoate; paraphens) with a cationic agent, such as CPC in relative amounts producing a polar charge that causes the composite to be adsorbed by the tissues being treated.

We have also found that a composition in accordance with the invention is especially effective as an anti-fungal rinse against a variety of Candida yeasts as well as *Torulopsis glabrata* and *Saccaromyces cerevisiae.*

When changes take place in host defense mechanisms and in the oral environment, then yeast or unicellular fungi may cause mucosal and periodontal opportunistic infections. The incidence of such infections has risen with the increase in the number of immunocompromised patients, such as those suffering from HIV infections, transplant recipients treated with immunosuppressive drugs and patients undergoing chemotherapy and radiation therapy for cancer.

In the article entitled "In Vitro Antifungal Properties of Mouthrinses Containing Antimicrobial Agents" by Giulana et al., in J. Periodontal 1997; 68:791–801 it is noted that mouthrinses containing an antimicrobial agent, such as Triclosan or CPC might serve as an appropriate alternative to conventional antifungal drugs in the management of oral candidiasis.

We have found, however, that far more effective as an alternative to conventional antifungal drugs is a composite mouth rinse in accordance with the invention in which a non-cationic antimicrobial agent is combined synergetically with a cationic antimicrobial agent. And we have found that this composite is also effective as a topical agent, in the form of an ointment or spray against superficial fungal infections.

This may include fungal infections of the head (*tinea capitis*), body infections (*tinea corporis*), "athletes foot" (*tinea pedis*) as well as groin and buttocks infections (*tinea crusis*). The composite has also been found to be effective against superficial candidiasis (moniliasis) and cutaneous candidiasis.

While there have been shown and disclosed preferred compositions in accordance with the invention for treating various infections, it is to be understood that many changes may be made in the composition without departing from the essential nature of the invention.

I claim:

1. A method for treating diseased tissues resulting from a herpes simplex virus infection giving rise to inflammation of the tissues and lesions comprising contacting said inflammation with a composition consisting essentially of:

A. a first antimicrobial agent constituted by Triclosan which is substantially water insoluble and non-cationic;

B. a second antimicrobial agent which is soluble in water and cationic;

C. a solubilizer in an amount sufficient to solubilize the Triclosan, the solubilized Triclosan being combined with the second agent to produce a composite that is polar and adsorbed and retained by the diseased tissues to which it is applied whereby the composition exhibits a high degree of substantivity, said composite applied to the diseased tissues being in an amount sufficient to alleviate inflammation thereof and to inhibit enlargement of said lesions.

2. A method as set forth in claim 1, in which the second agent is cetylpyridinium chloride.

3. A method as set forth in claim 1, in which the second agent is chlorhexidene.

4. A method as set forth in claim 1, in the form of an ointment which is applied topically to the diseased tissue.

5. A method as set forth in claim 4, in which the composite is disposed in an oil-water emulsion.

6. A method as set forth in claim 5, in which the emulsion is formed by intermingling water petrolatum, and an emulsifier.

7. A method as set forth in claim 6, further including a humectant.

8. A method as set forth in claim 7, further including a preservative.

9. A method as set forth in claim 8, in which the preservative is methyl paraben.

10. A method as set forth in claim 1, in which the percentage by weight of the second agent is in the range of about 0.001 to 3% and the percentage by weight of the first agent is in the range of about 0.010 to 5%.

* * * * *

UNITED STATES PATENT AND TRADEMARK OFFICE
CERTIFICATE OF CORRECTION

PATENT NO. : 5,855,872
DATED : January 5, 1998
INVENTOR(S) : Barry J. Libin

It is certified that error appears in the above-identified patent and that said Letters Patent is hereby corrected as shown below:

Column 5, line 32, after "cationic;" insert --and--.

Column 6, lines 1 and 2, delete "C. a solubilizer in an amount sufficient to solubilize the Triclosan,"; line 2, delete "solubilized".

Signed and Sealed this

Seventeenth Day of August, 1999

Attest:

Q. TODD DICKINSON

Attesting Officer

Acting Commissioner of Patents and Trademarks